United States Patent [19]

Daikuzono

[11] Patent Number: 5,290,280
[45] Date of Patent: Mar. 1, 1994

[54] LASER LIGHT IRRADIATION APPARATUS

[75] Inventor: Norio Daikuzono, Chiba, Japan

[73] Assignee: S.L.T. Japan Co., Ltd., Tokyo, Japan

[21] Appl. No.: 908,549

[22] Filed: Jun. 30, 1992

Related U.S. Application Data

[63] Continuation of Ser. No. 575,766, Aug. 31, 1990, abandoned.

[30] Foreign Application Priority Data

Sep. 8, 1989 [JP] Japan .................................. 1-233363

[51] Int. Cl.$^5$ .............................................. A61N 5/06
[52] U.S. Cl. ...................................... 606/16; 606/15; 606/17
[58] Field of Search ...................................... 606/7–18; 128/395, 397, 398

[56] References Cited

U.S. PATENT DOCUMENTS

| | | | |
|---|---|---|---|
| 3,050,907 | 8/1962 | Hicks, Jr. et al. | 385/115 |
| 4,126,136 | 11/1978 | Auth et al. | 606/16 |
| 4,233,493 | 11/1980 | Nath | 606/16 |
| 4,266,547 | 5/1981 | Komiya et al. | 606/15 |
| 4,402,311 | 9/1983 | Hattori | 606/14 |
| 4,664,467 | 6/1987 | Willett et al. | 606/12 |
| 4,693,244 | 9/1987 | Daikuzono | 606/16 |
| 4,693,556 | 9/1987 | McCoughan, Jr. | 606/15 |
| 4,736,743 | 4/1988 | Daikuzono | 606/16 |
| 4,799,479 | 1/1989 | Spears | 606/7 |
| 4,832,979 | 5/1989 | Hoshino | 606/16 |
| 4,848,339 | 7/1989 | Rink et al. | 606/7 |
| 4,860,743 | 8/1989 | Abela | 606/7 |

FOREIGN PATENT DOCUMENTS

| | | |
|---|---|---|
| 63-216579 | 9/1988 | Japan . |
| 2-34161 | 2/1990 | Japan . |
| 2185188 | 7/1987 | United Kingdom ................ 128/398 |

OTHER PUBLICATIONS

Nobori et al., "The Application of YAG LASER to Hyperthermia," *Bulletin of the Japan Society of Laser Medicine*, vol. 6, No. 3, Jan. 1986, pp. 71–78.

Suzuki et al., "Endoscopic Local Hyperthermia with Nd-YAG Laser—Experimental Study and Development of Computed Thermo-System," *Bulletin of the Japan Society of Laser Medicine*, vol. 6, No. 3, Jan. 1986, pp. 347–350.

Mashiko et al., "Basic Study on Phootchemical Effect of Phenophorbide as Irradiated by Nd:YAG Laser Light," *Bulletin of the Japan Society of Laser Medicine*, vol. 6, No. 3, Jan. 1986, pp. 113–116.

Dougherty et al., "Photoradiation Therapy for the Treatment of Malignant Tumors," *Cancer Research*, vol. 38 (Aug. 1978), pp. 2628–2635.

*Primary Examiner*—David M. Shay
*Attorney, Agent, or Firm*—Lowe, Price, LeBlanc & Becker

[57] ABSTRACT

A laser light irradiation apparatus for medical treatment of living tissues, a preferred embodiment, comprises a laser light emitter and plurality of optical fibers. The fore end portion of each optical fiber is exposed to form an exposed light emitting core. The exposed cores are surrounded by a clad-material serving as the laser light emitter in order to reduce power loss of the laser light. Also, since there is no space between the emitting face of the optical fiber and the impinging face of the emitter, a cooling fluid is not required to pass through. The laser light is emitted from the emitter to irradiate uniformly against the tissues, and if desired, against the tissues having a broad area. Further, a guide wire and a lead wire detecting a temperature can extend coaxially through the emitter. Therefore, a perforation of a normal part of the blood vessel can be prevented. To provide a more uniform power level distribution of the laser light, the optical fibers at the base portions are twisted.

21 Claims, 12 Drawing Sheets

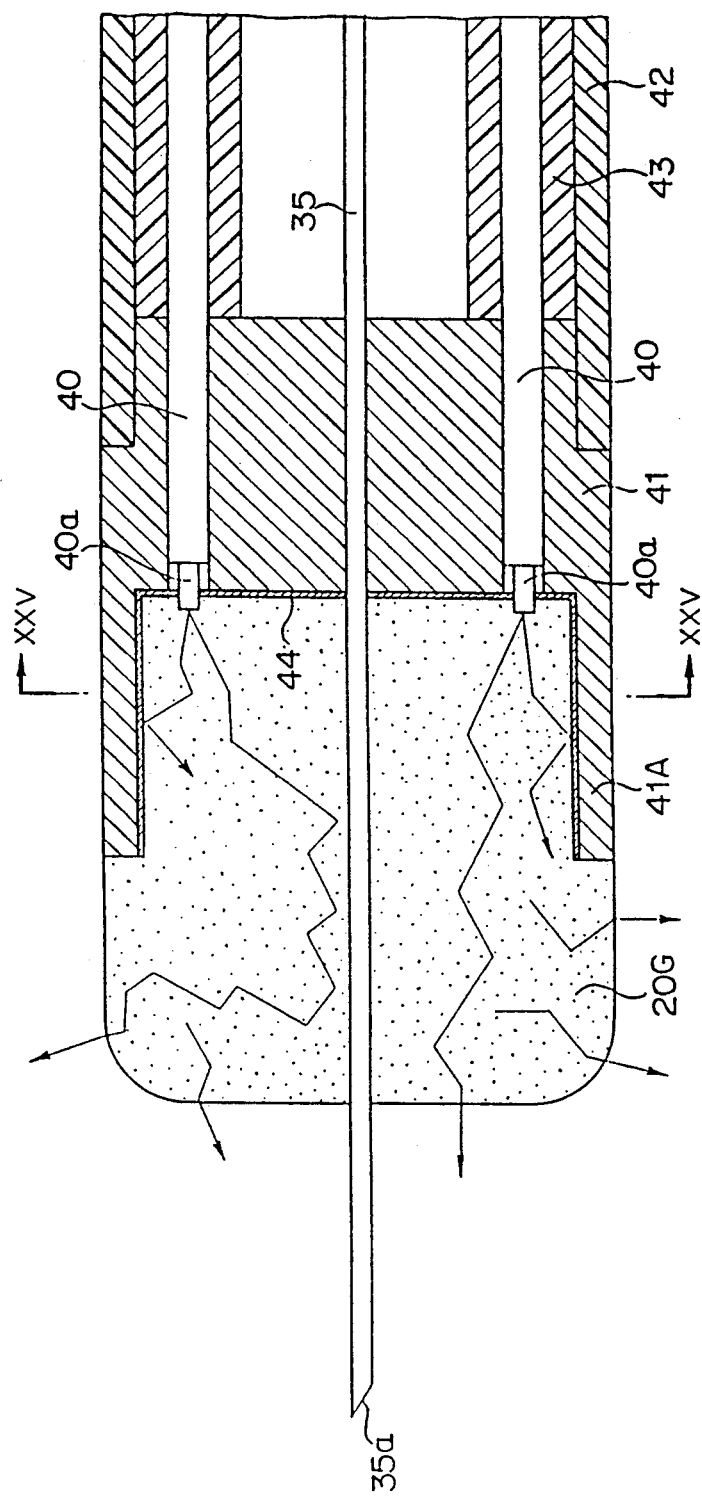

LASER LIGHT IRRADIATION APPARATUS

This application is a continuation of application Ser. No. 07/575,766 filed Aug. 31, 1990 now abandoned.

BACKGROUND OF THE INVENTION

1. Field of the Invention

This invention relates to a laser light irradiation apparatus, which irradiates laser light onto living tissues of an animal such as a human body for use in making an incision, vaporization of the living tissues or a thermal therapy and in case of widening a narrow path of the living tissues such as a stricture part caused by cholesterol formed in the blood vessel of the human body.

2. Prior Art

Medical treatments such as incisions of living tissues of animal organisms by irradiation with laser light are conspicuous due to the ability of such irradiation to provide hemostasis.

It had been the conventional method that the laser light was irradiated from the fore end of an optical fiber which is held out of contact with the living tissues. This method, however causes severe damage to the fore end portion of the optical fiber. Therefore, a method using a contact probe has been utilized as discussed below.

First, laser light is transmitted into an optical fiber, whose fore end portion is adjacent to treated living tissues. Next, the laser light fed out from the optical fiber is fed into an emitting probe, which is brought into or out of contact with the living tissues. Then, the laser light is emitted from the surface of the probe and irradiated against the living tissues. In this case, the probe should be brought into contact with the living tissues (hereafter "living tissue" is sometimes expressed by "tissue" only).

The inventor developed many kinds of contact probes which are utilized for various purposes.

When the contact probe of this type above described was used in the prior art, the fore end of an optical fiber was located so as to be apart from the back end face, that is an impinging face, of the probe. In this case, a physiological salt solution or pure air was passed through a gap formed between the optical fiber and a holder supporting the optical fiber, and through a space formed between the impinging face of the probe and the fore end of the optical fiber. Then, although the laser light having high power level impinged on this impinging face of the probe, this face could be cooled due to the passing of this fluid. Thus the damage of this face was prevented. Further, entry into the gap by pieces of living organism, a blood flow and the like, which might have occurred during a medical operation, could be prevented due to the passing of this fluid.

On the other hand, the inventor proposed, in Japanese Patent Application No. 63-171688, a laser light medical treatment equipment for burning off a stricture part caused by cholesterol formed on the inner wall of a blood vessel.

Before this invention, that is Japanese Patent Application No. 63-171688, for the treatment for the stricture part, a heat wire probe was inserted into the stricture part. Then, since the heat wire probe was heated as a whole, a normal blood vessel other than the stricture part could be damaged. Therefore, in order to prevent the normal blood vessel from being damaged, the laser light medical treatment equipment of this invention was proposed. According to this equipment, a laser light emitting probe is progressed through the blood vessel to a location before the stricture part formed in the blood vessel, and the laser light is emitted so as to irradiate only the stricture part, which is beyond the probe.

Further, lately, a localized thermal therapy is drawing special attention as a carcinostatic therapy. According to this method, cancer tissues are destroyed by keeping the cancer tissues at a temperature of about 42°–44° C. for 10–25 minutes by laser light irradiation. The effectiveness of this method has been reported by the inventors in the bulletin of Japan Society of Laser Medicine, vol. 6, No. 3 (January 1986) pp. 71–76 & 347–350.

On the other hand, considerable attention has been paid to laser-chemical therapies including the method reported in 1987 by Dougherty et al of the United States. According to this method, 48 hours after an intravenous injection of a hematoporphyrin derivative (HpD), weak laser-light such as argon laser or argon pigment laser is irradiated against a target area of the treatment, whereupon oxygen of the primary term which has a strong carcinostatic action is produced by HpD. There have been published various reports in this regard, including one in the bulletin of Japan Society of Laser Medicine, vol. 6, No. 3 (January 1986), pp 113–116. In this connection, it has also been known in the art to use "pheophobide a" as a photo-reactant. Further, recently, YAG laser has been put into use as a laser-light source.

In the above mentioned medical treatment, it is important that the laser light be irradiated uniformly for the cancer tissues and, in case of the thermal therapy, it is particularly important that the cancer tissues are heated uniformly.

Further, for heating the tissues uniformly, the inventor disclosed in Japanese Patent Application Laid-Open No. 63-216579 that an apparatus has plural number of laser light emitters and equipment for adjusting the power level of the laser light impinging into the emitters.

If laser light is irradiated against the tissues from an optical fiber directly or through the intermediary of a contact probe, the power level of the laser light irradiated against the tissues is the largest at a center position of an irradiated area on the surface of the tissues. The center position is contacted by the center of the optical fiber or that of the contact probe, then the power level decreases at positions on the surface of the tissues away from the center position.

For example, as shown in FIG. 28, when the laser light is irradiated against the tissues M with a contact probe P, the temperature distribution of this figure shows a distribution which is similar to a normal distribution. If the power level of the laser light is raised, the size of this temperature distribution is also enlarged to be a substantial similar figure. However, if the power level of the laser light is increased to an excess level, the tissues corresponding to the peak of the temperature distribution are damaged seriously. Accordingly, it is impossible that enlarging an irradiation area be carried out by only adjusting of the power level of the laser light.

Therefore, it is difficult to irradiate the laser light uniformly, and particularly more difficult to irradiate the laser light uniformly against the tissues having broad area. Accordingly, within the limit of the predetermined power level of the laser light, laser light irradiation against each small part of the tissues must be repeated many times in order to carry out the irradiation against all of the broad area the treated tissues. As a result, a medical operation can not be carried out quickly.

Under these circumstances, as described before, the inventor proposed in Japanese Patent Application Laid-Open No. 63-216579 providing a plural number of probes as the laser light emitters such that the laser light is irradiated from each probe simultaneously.

Although the laser light can be irradiated against the tissues having a broad area to some degree by provision of the plural number of laser light emitting probes, the necessity of the probes causes a problem as discussed below.

For forming the uniform temperature distribution on the irradiated tissues, the probes should be located at precise positions respectively in order to uniformly contact the tissues. Therefore, the medical operation can not be carried out quickly due to difficulty in precisely locating the probes. On the other hand, since each optical fiber should correspond to each probe, the size of the apparatus is large. Accordingly, this apparatus can not be used for a medical treatment in a narrow path in the tissues such as a catheter in a blood vessel.

On the other hand, in case of a treatment for a so-called angioplasty, which means burning off the stricture part formed on the inner surface of the blood vessel to widen the inside of the blood vessel, as described before, the inventor proposed the laser light irradiation probe. In this case, the probe can be used instead of the conventional heat wire probe and is inserted into the blood vessel along the flexible guide wire, which was inserted into the blood vessel previously. Further, in an embodiment of this proposal, in order to prevent the guide wire from being damaged by the laser light irradiation, the guide wire is placed so as to be deflected from the axis of the probe.

As shown in FIG. 29, deflection of the guide wire in relation to the axis of the probe causes the following problem. When a probe P is inserted in the blood vessel until the probe P reaches a bend in the blood vessel, due to the deflection of the guide wire, the probe P should be forced to be progressed further in the blood vessel against the original bending of the vessel. Therefore, the bending manner at this original bending of the blood vessel is changed to another bending manner. In this case, when the laser light is irradiated against the stricture part m, there is the fear of breaking of the wall of the normal part of the blood vessel BV other than the stricture part m or so-called perforation there.

The energy distribution of the laser light irradiation from the probe and the above mentioned temperature distribution shown in FIG. 28 have a common characterization. That is to say, in this energy distribution, there is a peak at its center while the level is gradually lowered at the both sides. Therefore, while the center of the stricture part m is completely burnt off, the inner wall of the stricture part m away from the center often still remains without being burnt off. Accordingly, the power level of the laser light should be raised in order to burn off the whole stricture part completely. However, if a normal part of the inner wall of the blood vessel faces the center of the emitting face of the probe due to the bending of the blood vessel, there is a risk that the normal part is burnt.

On the other hand, in the conventional apparatus where the fore end of the optical fiber is located so as to be apart from the back end face of the probe, there are the following problems:

(1) When the laser light impinges on the back end face of the probe from the fore end of the optical fiber, the impinging face of the probe is heated, thus; the cooling fluid should be supplied as explained before. Then, an equipment for supplying the fluid is necessary, resulting in an expensive apparatus. Further, a path of the fluid should be provided, thus the apparatus can not be designed so freely. The cooling fluid might flow into the tissues of a human body, thus; a bad effect is caused for the human body.

(2) The space formed between the fore end of the optical fiber and the back end face of the probe cause a power loss of the laser light. Accordingly, in order to compensate for this power loss, a large sized laser light generator is required.

(3) The cooling fluid is, as described before, also used for cleaning the fore end face of the optical fiber and the back end face of the probe. However, they are not cleaned sufficiently with the fluid, thus, damage caused by incomplete cleaning can not be prevented completely.

SUMMARY OF THE INVENTION

It is therefore a main object of the present invention to provide a small sized laser light irradiation apparatus, by which laser light can be irradiated against living tissues uniformly, if desired, against the living tissues having a broad area.

It is another object of the present invention to provide a laser light irradiation apparatus, in which a guide wire and a lead wire detecting a temperature are provided so as to be coaxial with a laser light emitter.

It is still another object of the present invention to provide a laser light irradiation apparatus, in which the power loss of the laser light is very low and in which the supplying of a cooling fluid is not required.

In order to solve the above mentioned problems, a laser light irradiation apparatus of the present invention comprises the plural number of optical fibers and a laser light emitter. Each optical fiber transmits laser light fed from a laser light generator, and at least the fore end portion of each optical fiber comprises an exposed core. Then, the exposed cores are surrounded by a clad-material serving as the laser light emitter.

In order to make a flat power level distribution of laser light irradiation, according to a laser light irradiation apparatus of the preferred embodiment of the present invention, the arrangement of the optical fibers at their base portions is different from the arrangement of the optical fibers at their fore end portions.

In the present invention, at least the fore end portion of the optical fiber is exposed to form a core. Then, the cores are surrounded by the clad-material serving as the laser light emitter.

Accordingly, the laser light emitted from the fore end of the optical fiber impinges into the clad-material directly. Then, the power loss of the laser light is not produced at all between the emitting face of the optical fiber and the impinging face of the clad-material. Therefore, the laser light generator having a low power level can be used resulting in a low cost. In the prior art, damage was caused by the pieces of the living organism and the blood entering the space between the optical fiber and the laser light emitter. However, since the fore end portion of the optical fiber is buried in the clad-material, such damage is not caused. Further, in the present invention, the impinging face of the laser light emitter, that is the clad-material, is not heated; thus, the supplying of the cooling fluid is not required. As a result, the above mentioned problems are solved by this present invention.

Further, according to the present invention, the plural number of optical fibers are provided so that their fore end portions are buried in the material of the laser light emitter, that is the clad-material. Therefore, in each power level distribution of the laser light irradiation from the emitting face of the laser light emitter, there is a peak at each axis of each optical fiber. That is to say, as shown in FIG. 1, a whole energy distribution, which is produced by combining each energy distribution, shows a uniform and broad energy distribution.

In a preferable embodiment described hereinafter, the base portions of the optical fibers are twisted or distorted so that the arrangement of the optical fibers at their base portions is different from the arrangement at their fore end portions. Therefore, even if power distribution of the laser light fed into each optical fiber with each distribution is similar to a normal distribution, the power level distribution of the laser light irradiation from the laser light emitter, as a whole, shows a flat distribution due to randomization of laser light transmitting paths caused by this twisting or distorting.

On, the other hand, for the angio-plasty in the conventional art, only structures at the center part of a blood vessel were mainly burnt off. However, by the present invention, the laser light is emitted also from the circumferential part of the fore end face of the emitter. Therefore, the strictures along inner wall of the blood vessel, as well as the center part, can be burnt off surely. Due to this complete burning, laser light emission with high power level is not required. Further, even if the blood vessel is bent such that the normal part of the inner wall of the blood vessel faces the center position of the emitting face of the emitter, since the power level of the laser light irradiation is not so high, there is no fear of perforation at the normal part of the blood vessel.

In case of a thermal therapy, since the tissues having a broad area are heated uniformly, this therapy can be performed quickly and there is no fear that the tissues at a center position of the irradiated area is damaged seriously.

On the other hand, by forming a through-hole along the axis of the laser light emitter, the laser light is not emitted from a center part of the fore end face of the emitter. Accordingly, from the view of the whole power level distribution of the laser light irradiation, the laser light is emitted more uniformly. Further, the guide wire can be inserted through the through-hole, thus, the guide wire can be provided at the center of the probe. Therefore, when the emitter is inserted along the guide wire, the emitter can be always located at the center of the blood vessel as shown in FIG. 22. Therefore, the blood vessel is not forced to be bent, and the perforation, which might be caused by to the bending of the blood vessel and the laser light irradiation against the normal part of the blood vessel, does not occur.

With this apparatus, the thermal therapy can also be performed efficiently. That is to say, the lead wire detecting the temperature, for example by means of a thermocouple, can be inserted through the through-hole so that the tip end of the lead wire can be pushed into the center of the target area to detect the temperature there for the efficient thermal therapy. However, in the prior art, since a thermocouple was provided so as to pass around and attach along the side of a probe (emitter), the thermocouple was set to be inserted into a position deflected from the center of the irradiated target area. Comparing the prior art, in the present invention, as described above, the thermal therapy can be performed under the precise temperature control due to the suitable location of the lead wire.

While plural pairs of optical fibers and probes were provided in the conventional apparatus, in the apparatus of the present invention, plural number of optical fibers correspond to one emitter. Accordingly, although this apparatus also has also plural optical fibers, the size of this apparatus is smaller than the conventional apparatus. Therefore, the apparatus can be inserted into a narrow path of organisms.

Further objects and advantages of the present invention will be apparent from the following description, reference being made to the accompanying drawing wherein preferred embodiments of the present invention are clearly shown.

BRIEF DESCRIPTION OF THE DRAWINGS

FIG. 24 is a longitudinal sectional view of an important part of an irradiation, which is modified from the first embodiment;

DESCRIPTION OF THE PREFERRED EMBODIMENT

The present invention is described more particularly below with reference several preferred embodiments.

Figure 1:
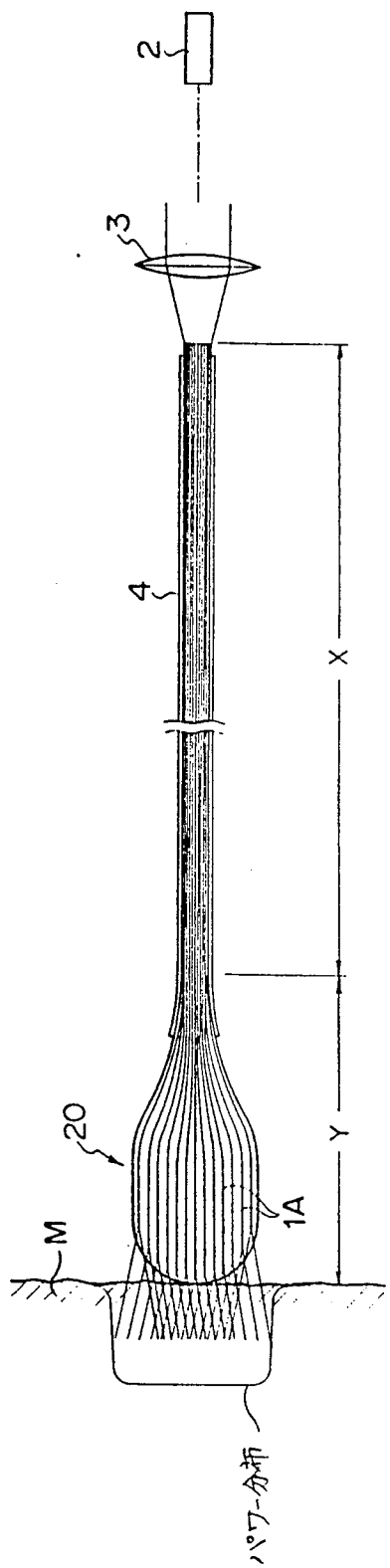
FIG. 1 is a longitudinal sectional view of an irradiation apparatus in a first embodiment related to the present invention.
Figure 3:
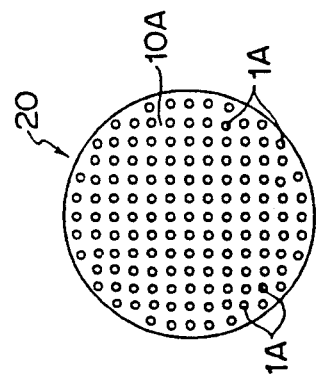
FIG. 3 is a sectional view taken on line III—III of FIG. 2.
Figure 2:
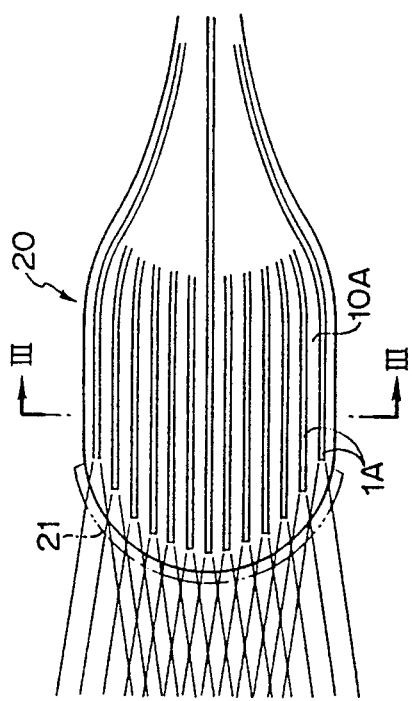
FIG. 2 is an expanded sectional view of an important part of FIG. 1.

FIGS. 1, 2 and 3 show a first embodiment of a laser light emitting apparatus connected to an endoscope. A plurality of optical fibers for example four or more, and preferably ten or more, compose a base portion X as a laser light transmitting part and a fore end portion Y as a laser light emitting part, although a boundary between these two portions X and Y can not be shown in this figure.

Figure 4:
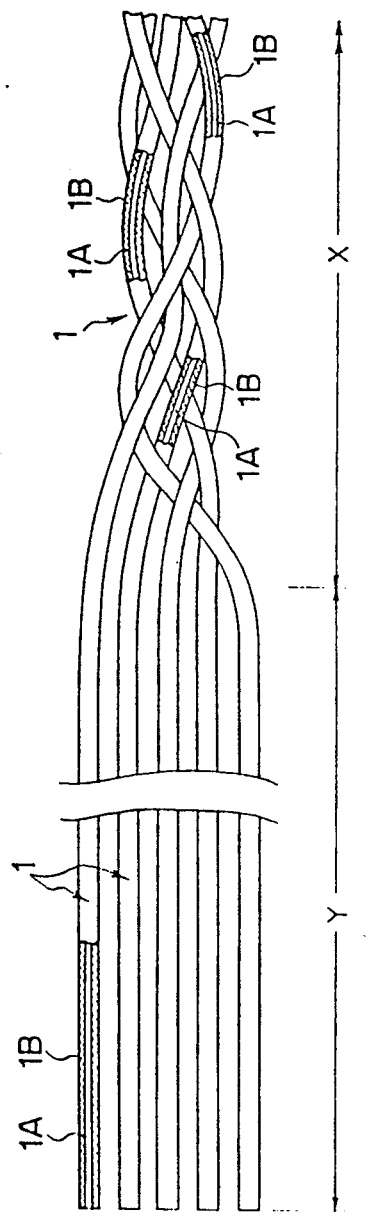
FIG. 4 is an elevational view showing the producing operation of the apparatus of FIG. 1 in a preparation stage.
Figure 5:
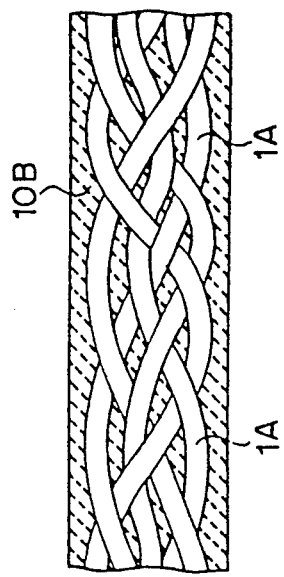
FIG. 5 is a longitudinal sectional view of a laser transmitting part of an apparatus.

For explaining the composition of this apparatus clearly, the producing method of this apparatus will be explained previously. First, as shown in FIG. 4, original optical fibers 1 are prepared. Each original optical fiber 1 has a core 1A and a clad 1B surrounding the core 1A. Then, while at the base portion X, the fibers 1 are twisted in an irregular manner, the twisted original optical fibers 1 at the base portion X are heated to a temperature which is substantially the same temperature as or higher temperature than the melting point of the clad 1B and which is lower temperature than the melting point of the core 1A. Then, at the base portion X, the clads 1B of original optical fibers 1 are moulded to be one clad 10B, which includes the twisted cores 1A as shown in FIG. 5.

On the other hand, at the fore end portion Y, the original optical fibers 1 are not twisted but arranged in parallel separately. A clad-material 10A is heated to a temperature, which is the same as or higher than the melting point of the clad 1B and which is lower than the melting point of the core 1A, to be melted. Then, the optical fibers 1 arranged in parallel are dipped in the melted clad-material 10A to a predetermined depth, at which the laser light can be penetrated. As so doing, since the clad-material 10A is heated, the clads 1B can be melted to be mixed into the clad-material 10A. In this case, the clad 1B and the clad-material 10A are fabricated from materials which have similar compositions so that they can be molded to be one substance easily. For example, these materials are same quartz or two kinds of quartz which differs in only melting point. Further, the core 1A is preferably fabricated from a material, which is also similar to the material of the clad 1B and the clad-material 10A. Therefore, in this embodiment, quartz can be used as a suitable material of the core 1A.

As a result, a laser light emitter 20 composing the resulting clad-material 10A and the number of cores 1A, which are arranged in parallel and which are included in the clad-material 10A. The clad-material 10A includes also the melted clads 1B. However, since the boundary between the clad-material 10A and each clad 1B is not clear, the clads 1B are not shown in this figure.

The shape of the laser light emitter 20 corresponds to the shape of a container including the clad-material 10A. For example, as shown in FIG. 1, if the container has a constriction at the back end of the emitter 20, the shape of the laser light emitter 20 should be provided with an open having an inner diameter corresponding to the diameter of the constriction.

The laser light irradiation apparatus of this type described above is used as follows. First, laser light fed from a laser light generator 2 goes through an impinging lense 3. Next, the laser light from the lense 3 is impinged from the back end face of each twisted core 1A. Then, the impinged laser light is transmitted in each core 1A to be emitted from the fore end face of each core 1A. Further, the emitted laser light goes through the clad-material 10A to be emitted from the fore end of the laser light emitter 20. Finally, the emitted laser light is irradiated against treated tissues M.

In this case, when the laser light is impinged from the back end of each twisted core 1A, the power level distribution of the impinged laser light shows a distribution which is similar to a normal distribution. However, the arrangement of the cores 1A is randomized due to this twisting of the cores 1A; for example, the core 1A locating at the center part is twisted so as to locate at the circumferential part and another core 1A locating at the circumferential part is twisted so as to locate at the center part. Accordingly, as shown in FIG. 1, the power level distribution of laser light emission from the emitter 20 shows a uniform distribution.

In FIG. 1, the emitting face of the emitter is not covered by anything. However, as shown by an imaginary line in FIG. 2, a surface layer 21 or a scattering layer, which will be explained after, can be formed on the emitting face of the fore end portion of the emitter 20. The emitter, whose emitting face is not covered by anything, is used for mainly coagulation and heating of the tissues. On the other hand, the emitter, whose emitting face is covered with the surface layer 21, is used for mainly vaporization of the tissues.

The above mentioned base portion X as the laser light transmitting part can be coated with a protection tube 4 fabricated from a synthetic resin material and the like.

In the present invention, the emitter having several kinds of shapes can be applied. There are, for example, a cylindrical-shaped emitter 20A having a flat emitting face as shown in FIG. 6, a knife-shaped flat emitter 20B as shown in FIGS. 7 and 8, a hook-shaped flat emitter 20C as shown in FIG. 9, claw-shaped emitters 20D as shown in FIGS. 14, 15, 16 and 17, a sickle-shaped emitter 20E as shown in FIGS. 18, 19, 20 and 21.

Figure 6:
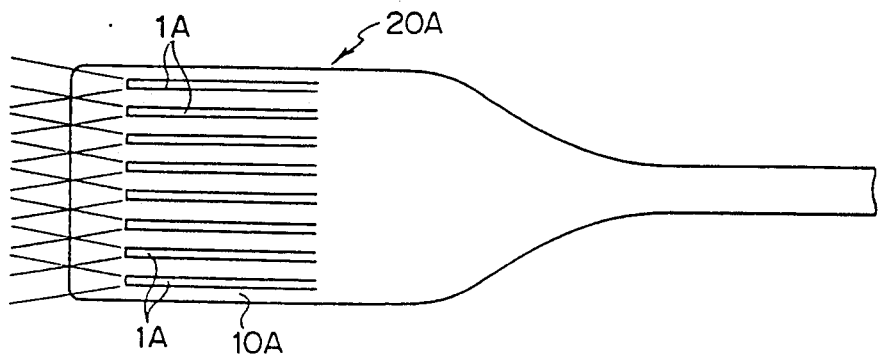
FIG. 6 is a longitudinal sectional view of an important part of a laser light emitter related to the present invention.

The emitter 20A of FIG. 6 is used for the coagulation, the heating and the vaporization of the tissues like the emitter 20 of FIG. 1.

Figure 7:
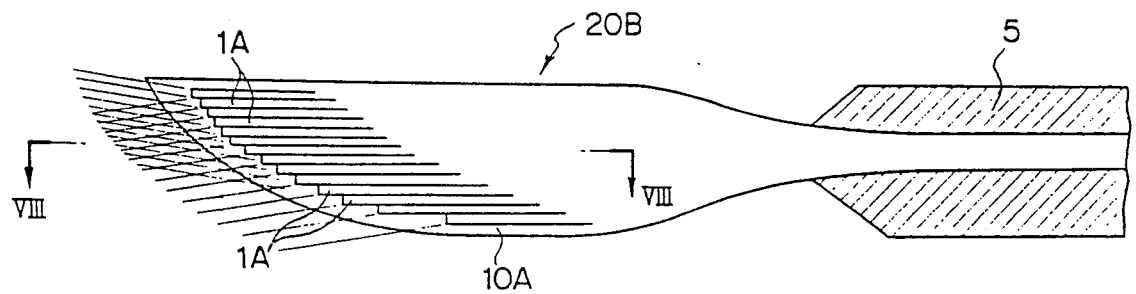
FIG. 7 is a longitudinal sectional view of an important part of another laser light emitter.
Figure 8:
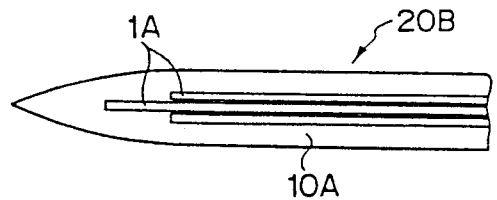
FIG. 8 is a sectional view taken on line VIII—VIII of FIG. 7.

In the emitter 20B of FIGS. 7 and 8, the cores 1A of the optical fibers are gathered to be a substantial straight line. Then, the emitter 20B is used surgically for the incision and the vaporization of tissues. The above mentioned surface layer can be formed on the knife-shaped face, that is the tapered face, of the emitter 20B. A handle 5 is attached to its back end portion.

Figure 9:
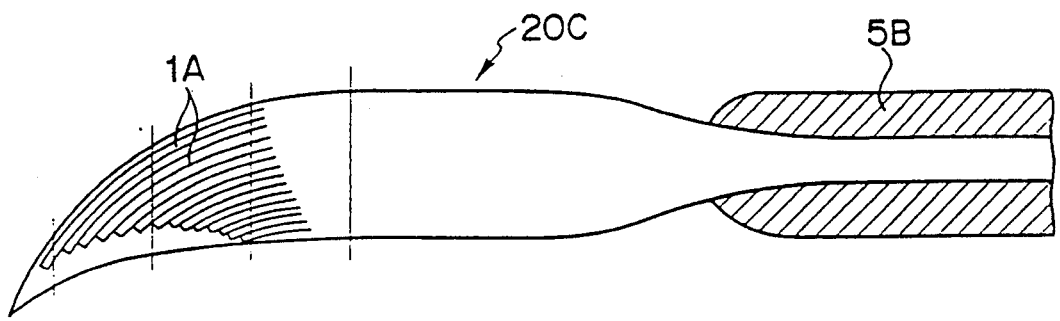
FIG. 9 is a longitudinal sectional view of an important part of still another laser light emitter.
Figure 11:
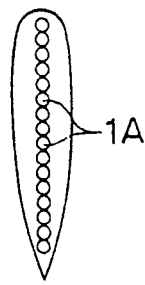
FIGS. 10, 11, 12 and 13 are side views taken on the four lines of FIG. 9.
Figure 10:
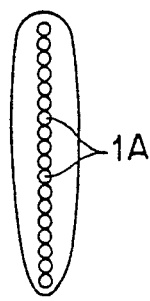
Figure 13:
Figure 12:
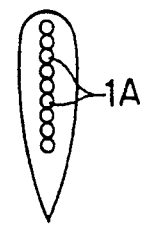

The emitter 20C of FIG. 9 is also used for mainly in a surgical treatment for the incision and the vaporization of tissues.

Figure 14:
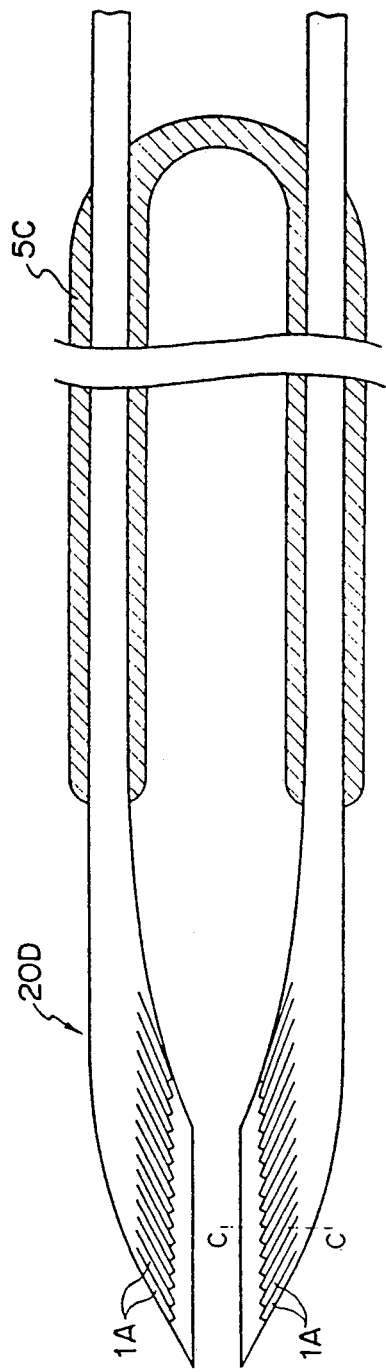
FIG. 14 is a longitudinal section view of an important part of a laser light emitter having a claw-shape.
Figure 15:
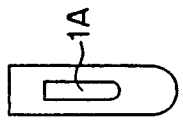
FIGS. 15, 16 and 17 are sectional views having several shapes respectively taken on line C—C of FIG. 14.
Figure 16:
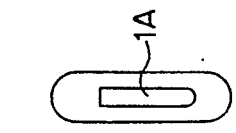
Figure 17:
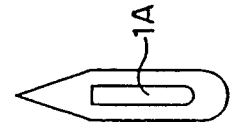
Figure 18:
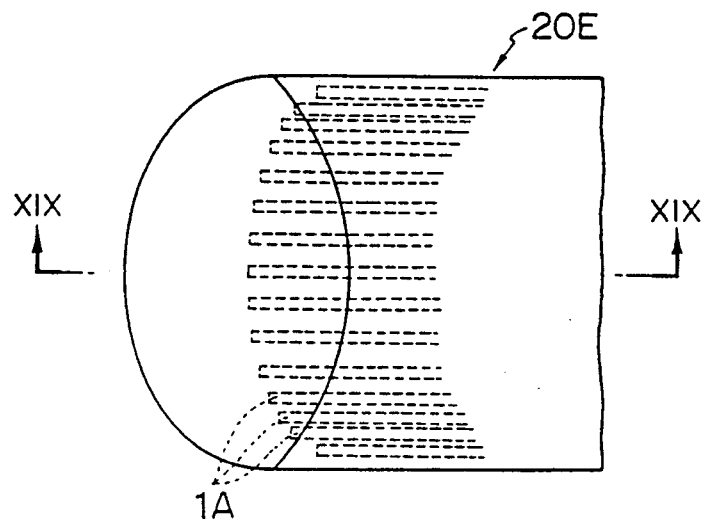
FIG. 18 is a plan view of the fore end portion of a laser light emitter having a chisel-shape.
Figure 19:
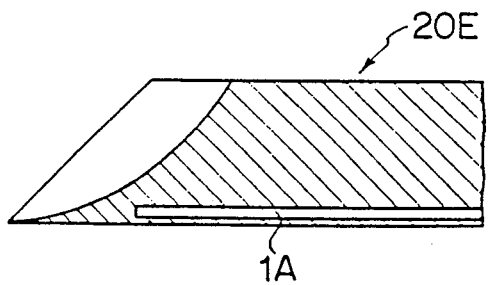
FIG. 19 is a sectional view taken on line XIX—XIX of FIG. 18.
Figure 21:
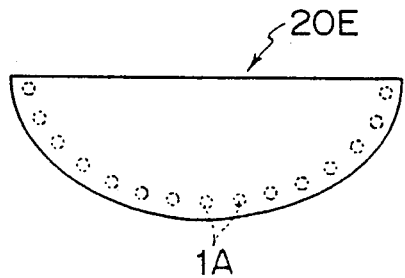
FIG. 21 is a side view of FIG. 18.
Figure 20:
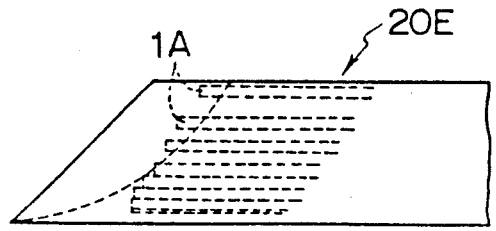
FIG. 20 is an elevational view of FIG. 18.

In the emitter 20D of FIG. 14, a pair of emitting parts are provided to be faced each other. The emitter 20D is located so that the two emitting parts pinch the tumor of tissues. The emitter 20D whose emitting face is flat and covered by nothing as shown in FIG. 15 is used mainly for coagulation, whose emitting face is rounded off and covered with the surface layer explained hereinafter as shown in FIG. 16 is used mainly for vaporization and whose emitting face is tapered and covered with the surface layer as shown in FIG. 17 is used mainly for incision respectively. A grip handle 5C is provided at the back portion of the emitter 20D and can be operated with a restoring force.

The sickle-shaped emitter 20E of FIGS. 18, 19, 20 and 21 is used for mainly removing a tumor formed in a narrow path of organisms. In this case, the emitter 20E is inserted to be progressed in the direction of its axis.

Figure 22:
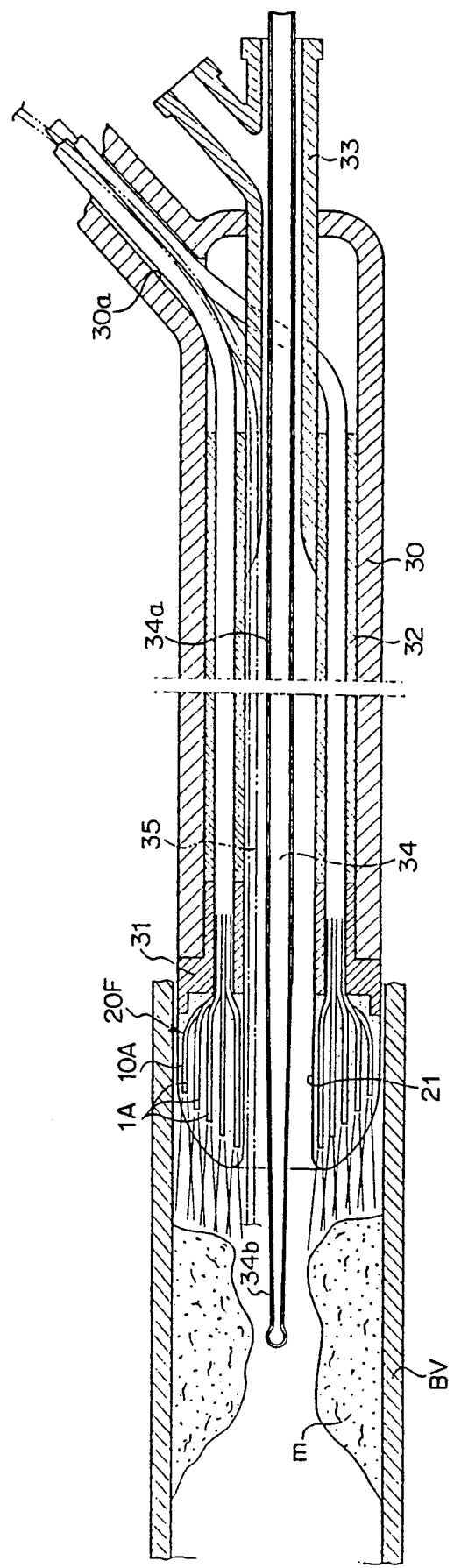
FIG. 22 is a longitudinal sectional view of an embodiment of an apparatus used for angio-plasty.

On the other hand, FIG. 22 shows an embodiment used mainly for the treatment of angio-plasty. An emitter 20F is formed to be ring-shaped and has a fore end face being rounded off at its circumference. Therefore, the emitter 20F can be progressed in a blood vessel with a small refraction with the inner wall of the blood vessel. The emitter 20F can be fabricated in the basically same manner as the above mentioned producing method, although the producing method of this embodiment differs in that a laser light transmitting part can be connected optically to a laser light generator by dividing the whole of optical fibers to, for example, four groups. A main tube 30 is fabricated from a flexible material such as the resin of tetrafluorethylene and the like. The emitter 20F and the main tube 30 are connected through the intermediary of a metal holder 31.

Each laser light transmitting part is inserted into the main tube 30 from an inserting hole 30a. Then, the fore end portion of the transmitting part is supported and surrounded by the holder 31. The base portion or the back side portion of the transmitting part in the main tube 30 is supported and surrounded by a synthetic resin holder tube 32.

On the other hand, a through-hole 21 is formed to go through along the axis of the emitter 20F to communicate with the inner through-hole of the holder 31 and the holder tube 32. A conductive tube 33 is provided in the main tube 30 so as to be projected from the back end of the main tube 30. The tip end of the conductive tube 33 is inserted into the inner side of the holder tube 32. A guide wire 34 is inserted through the conductive tube 33, further through the inner side of the holder tube 32 and that of the holder 31 so as to be projected from the through-hole 21 of the emitter 20F. The base portion of the guide wire 34 is coated by a synthetic resin coating such as the resin of tetrafluoroethylene. The fore end portion of the guide wire 34 is tapered gently and is totally gold plated 34b.

This laser light irradiation apparatus is used as follows;

First, before surgical insertion into a human body, the guide wire 34 is inserted through the apparatus. Next, the guide wire 34 is further inserted into the treated blood vessel BV so that the tip end of the guide wire 34 is proceed further than a stricture part m, which will be burnt off by laser light irradiation.

Then, the apparatus other than the guide wire 34 is inserted in the blood vessel BV along the guide wire 34 so as to proceed until the external surface of the fore end portion of the emitter 20F is adjacent to the stricture part m. Laser light is fed into the core 1A of each optical fiber to be emitted from the emitter 20F mainly from the external surface of the fore end portion. Finally, the laser light is irradiated against the stricture part m.

By the laser light irradiation, the stricture part m is burnt off to widen the inside of a blood vessel. In this case, if desired pressurized air or pressurized liquid is sent into a well-known balloon, thus, the balloon is expanded and press the stricture part m. As so doing, together with the above mentioned burning off the inside of the blood vessel by the laser light irradiation, the stricture part m can be broken mechanically.

As shown in FIG. 22, in this embodiment, the laser light is emitted from the circumference of the fore end face of the emitter 20F. Therefore, the laser light is irradiated efficiently against the stricture part m formed on the inner wall of the blood vessel BV. Accordingly, the stricture part m can be burnt off sufficiently even if the power level of the laser light is low.

When the laser light is irradiated against the stricture part m, the laser light also is irradiated against the projecting part of the guide wire 34. Therefore, the surface of the fore end portion of the guide wire 34 is coated by a gold plating layer 34b for preventing the surface from being damaged.

Figure 23:
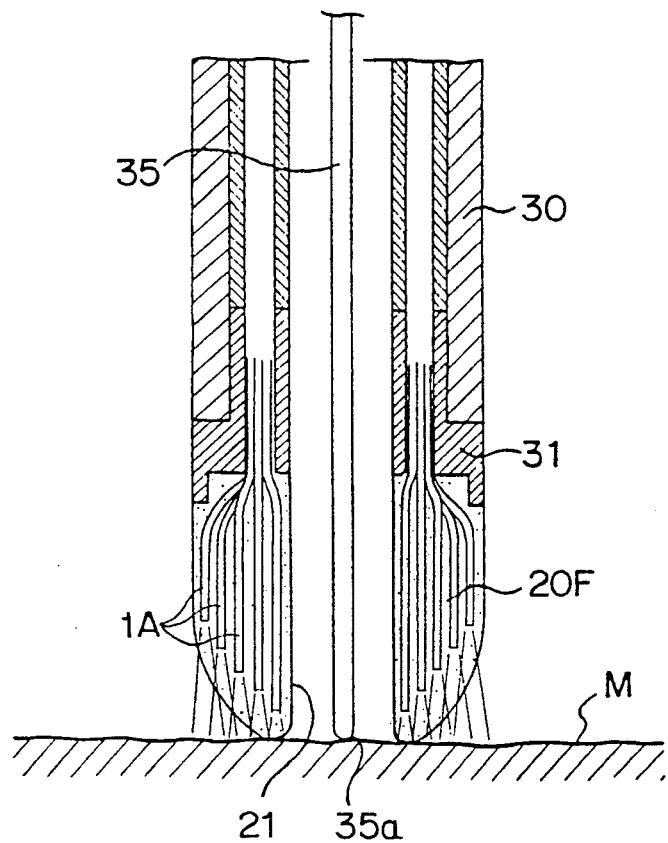
FIG. 23 is a longitudinal sectional view of an important part of an irradiation apparatus carrying out a thermal therapy.
Figure 28:
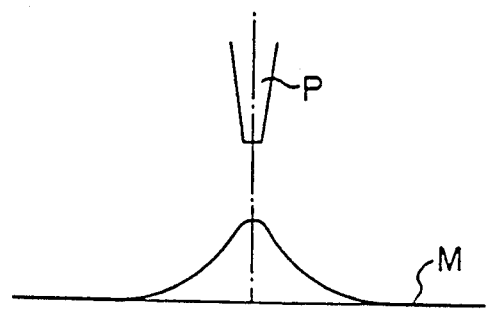
FIG. 28 is a schematic illustration for a power level distribution of laser light irradiation with a laser light emitter.

The apparatus of FIG. 22 is used for also a thermal therapy efficiently. As shown in FIG. 23, a lead wire 35 detecting a temperature having a thermocouple 35a at its tip end is brought into contact with the surface of cancer tissues M or is pushed into the cancer tissues M. Then, the emitter 20F is brought into contact with the surface of the cancer tissues M. As so doing, the laser light having a low power level is irradiated against the tissues M. In this case, the power level of the irradiated laser light can be controlled so as to keep the tissues M at the temperature of about 42°–44° C.

Figure 25:
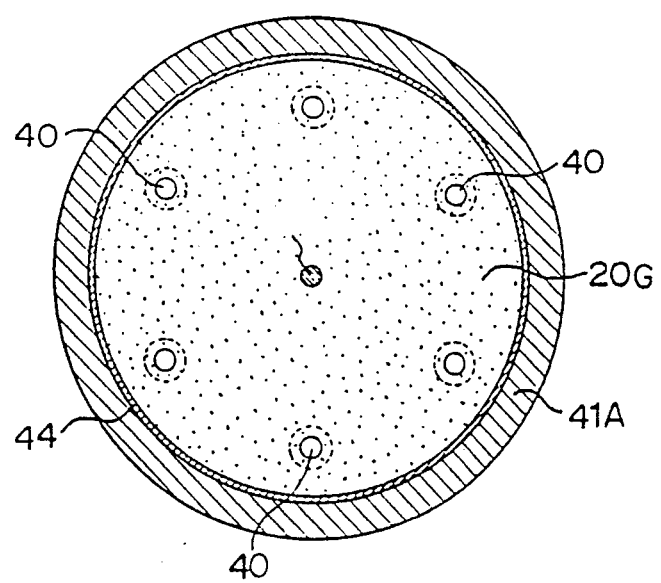
FIG. 25 is a sectional view taken on line XXV—XXV of FIG. 24.

In the above mentioned embodiments, the emitters are fabricated from ceramic such as quartz and the like. However, in the embodiment of FIGS. 24 and 25, an emitter 20G fabricated from a synthetic resin material is used. This emitter 20G is connected to a flexible protection tube 42 fabricated from the resin of tetrafluoroethylene and the like through the intermediary of a metal holder 41 having a sleeve-like connector 41A.

A supporting tube 43 fabricated from a synthetic resin material is provided to be connected to the holder 41 on the inner side surface of the protection tube 42. In the supporting tube 43, for example, six optical fibers 40 are supported so as to surround the axis of the tube 43. Each optical fiber 40 is optically connected to a laser light generator (not shown). A lead wire 35 detecting a temperature having a thermocouple 35a at its tip end is inserted through the holder 41 and the emitter 20G so as to be projected from the fore end portion of the emitter 20G. Then, the lead wire 35 is connected to a temperature measuring unit (not shown). Then, according to the result of detecting the temperature, the power level of the laser light, which is fed into the optical fiber 40 from the laser light generator, should be controlled. This controlling is carried out by, for example, adjusting a timer switch, which is provided between the laser light generator and the back end of the optical fiber 40.

The emitter 20G composes a substantial cylindrical part having a fore end face being rounded off at its circumference and another cylindrical part at the back side of the emitter 20G having a smaller radius than that of the substantial cylindrical part by the thickness of the holder 41. These two cylindrical parts are fixed integrally. The smaller cylindrical part of the emitter 20G is fitted in the sleeve-like connector 41A. Adding to this fitting, if desired, by using an adhesive between the mating surfaces; a back end circumferential face of the larger cylindrical part of the emitter 20G and the fore end circumferential face of the sleeve-like connector 41A for high strength in fixing.

A laser light reflective layer 44 is formed on the mating surfaces of the emitter 20G and the holder 41, in this embodiment the circle fore end face of the holder 41 and the inner side face of the sleeve-like connector 41A. Although the reflective layer 44 is preferably gold plated to give a high heat resistance, it might be aluminum plated and the like in view of the material of the layer. For forming the layer, vapor-deposit as well as plating can be used.

Further, the fore end portion of the above mentioned optical fiber 40 is inserted to be buried in the material of the emitter 20G and the fore end face of the core 40a of each optical fiber 40 is contacted with the material of the emitter 20G directly without any gap.

The emitter 20G of this embodiment contains laser light scattering particles and is fabricated from the laser light penetrating synthetic resin material. The material is synthetic resin such as silicone resin, acrylic resin (more preferably, methyl methacrylate resin), carbonate resin, polyamide resin, polyethylene resin, urethane resin, polyester resin and the like, more preferably, thermoplastic synthetic resin. For the laser light scattering particles, the material, which has a larger refractive index for the laser light than that of the above mentioned synthetic resin material of the emitter, is used, for example, a natural or an artificial material such as diamond, sapphire, quartz material, single crystal zirconium oxide, laser light penetrating synthetic resin having heat resistance (it is needless to say that it is different from the above mentioned synthetic resin material of the emitter), laser light reflective metal (such as gold, aluminum and the like), and the particles on whose surface the above mentioned laser light reflective metal are coated to be a compound material.

On the other hand, if desired, in case that the emitter contains laser light absorbing particles such as carbon, graphite, iron oxide, manganese dioxide and the like together with the scattering particles, while the laser light is scattered in the emitter to be emitted from the emitter, the laser light is impinged on the absorbing particles to generate heat energy to give a large effect of heating.

The above mentioned emitter 20G of this embodiment is fabricated by moulding to be a desired shape from the synthetic resin material, which is in a melted state and into which the scattering particles are dispersed. As so doing, the fore end portion of the optical fiber 40 is buried in the material of the emitter 20G as shown in FIG. 24, and the middle part of the lead wire 35 detecting the temperature is buried in the material of the emitter 20G so as to be fixed integrally to the emitter 20G. Accordingly, for fabricating this apparatus, for example, the holder 41 is made easily by molding from one mould to which the material is poured, while the optical fiber 40 and the lead wire 35 are projected from the fore end circle face of the holder 41.

The laser light irradiation apparatus of the type described above in the present invention is used, for example, in a following manner. The laser light is generated from the laser light generator, while the apparatus connected to an endoscope is surgically or physically inserted to a treated target area in a human body. The laser light from the laser light generator is fed into the back end of each optical fiber 40 and is transmitted therein to be emitted from the fore end face of the core 40a. Then, the emitted laser light is fed into the emitter 20G directly, penetrates therein and is emitted from its external surface, while the laser light is repeated refracted from the scattering particles in the emitter 20G. Therefore, as shown in FIG. 24, the laser light, after the repeated refraction, is emitted from the external surface of the emitter 20G uniformly for irradiation of the tissues. As so doing, as shown in FIG. 24, the laser light reaching at the internal surface of the sleeve-like connector 41A is reflected on the reflection layer 44. Therefore, the sleeve-like connector 41A and the metal holder 41 are prevented from being heated and from being damaged. Further, the reflected laser light is brought to go forward.

Laser light irradiation of this embodiment is carried out in the same manner as that of the above embodiment of FIG. 23. That is to say, while the external surface of the fore end portion of the emitter 20G is brought into contact with cancer tissues M, the projecting portion of the lead wire 35 from the external surface of the fore end portion of the emitter 20G, is pushed into the tissues M. Then, the temperature of the tissues M is detected with the thermocouple 35a for controlling the power level of the laser light fed into the optical fiber 40; in other words, the power level of the laser light emitted from the external surface of the emitter 20G, as described before. Then, the cancer tissues M are destroyed by keeping the tissues M at the temperature of about 42°–44° C.

As a modified embodiment of the embodiment of FIG. 24 and the like, each optical fiber 40 including a clad surrounding the core and the exposed core 40a can be buried in the material of the emitter 20G.

On the other hand, the laser light is irradiated against also the lead wire 35 detecting the temperature. Therefore, in order to prevent the lead wire 35 from being heated and from being damaged, the wire 35 is preferably coated with a laser light reflecting layer such as a gold plated layer and a titanium coating layer like the synthetic resin material coating 34a and the gold plated layer 34b on the above mentioned guide wire of FIG. 22.

Figure 26:
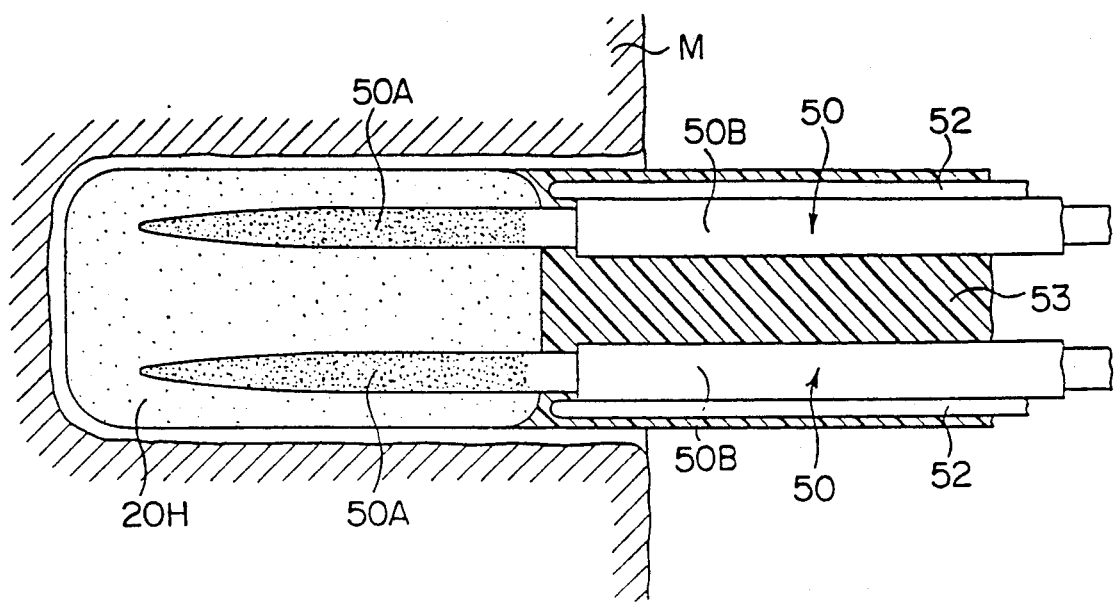
FIG. 26 is a longitudinal sectional view of an important part of an irradiation apparatus in another embodiment.
Figure 27:
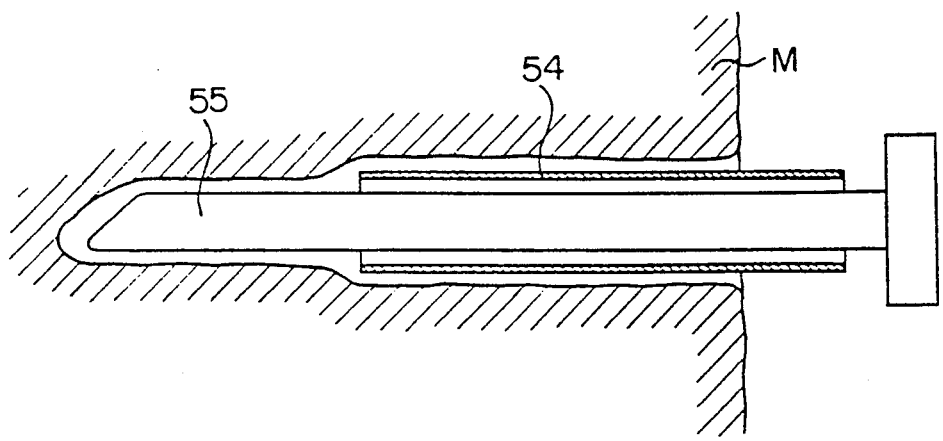
FIG. 27 is a longitudinal sectional view showing an operation for forming an inserting guide prior to inserting of the apparatus of FIG. 26 into tissues.
Figure 29:
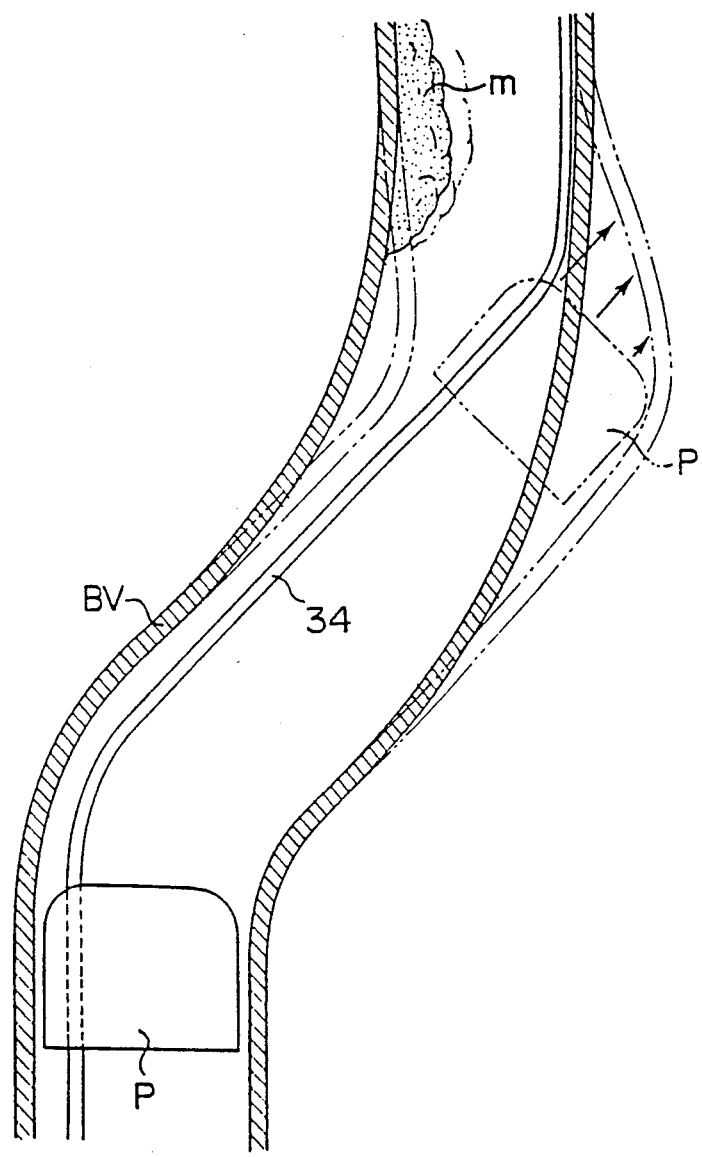
FIG. 29 is a longitudinal sectional view showing a embodiment as a reference of a medical treatment for a blood vessel having a stricture part.

FIG. 26 shows another embodiment. The apparatus of this embodiment is used effectively in a treatment not for the surface of tissues but for inside of the tissues.

An emitter 20H and plural number of optical fibers 50 are provided in this apparatus. At the fore end portion of each optical fiber 50, a clad 50B is removed so that a core 50A is exposed. The tip end of the core 50A is tapered. A laser light scattering layer is formed on almost all of the external surface of the core 50A. In this figure, this laser light scattering layer is directed by marking dots. For forming this scattering layer, first, ceramic powders such as silicon dioxide and the like are sprayed and heated to a temperature which is slightly lower than its melting point. Therefore, the original sprayed powders do not become to be homogeneous due to incomplete heating. Then, these incompletely heated ceramic powders are cooled. Accordingly, the laser light scattering layer can be formed on the core 50A, where the powders partly melt and partly remain. Due to this scattering layer, when the laser light is emitted from the external surface of the core 50A, the laser light impinges on each resulting ceramic powder with refraction to be scattered.

On the other hand, the emitter 20H is provided so that the cores 50A, each of which is covered with this scattering layer, are buried in the material of the emitter 20H. The material of the emitter 20H is fabricated from synthetic resin containing scattering particles in the same manner as the embodiment of FIG. 24.

Lead wires 52 detecting temperatures are provided to be connected to the cores 30B respectively. The external surface of each lead wire 52 is gold plated. Then, the tip end of each lead wire 52 locates adjacent to the back end face of the emitter 20H. The lead wires 52 together with the optical fibers 50 are surrounded by a flexible sheath 53, which is fabricated from synthetic resin such as polyethylene, urethane and the like, silicone rubber and so on. By molding, the sheath 53 is fixed integrally to the lead wires 52, the optical fibers 50 and the emitter 20H.

In case of applying this apparatus of this embodiment, as shown in FIG. 26, first, a so-called puncture needle 55 together with a guide tube 54 is inserted into the tissues M such as lever tissues. Next, only the puncture needle 55 is removed. Then, instead of the needle 55, the fore end portion of this laser light irradiation apparatus is inserted into the tissues M so as to go through the guide tube 54. Then, the laser light is fed into each optical fiber 50 to be emitted from each core 50A provided at the fore end portion of the optical fiber 50. As so doing, the laser light is scattered in the scattering layer covering each core 50A. Then, the scattered and emitted laser light is fed into the emitter 20H and goes through it, while the laser light repeats to be scattered with the scattering particles in the emitter 20H. At last, the laser light is emitted from the external surface of the emitter 20H uniformly. This apparatus is applied for a local thermal therapy for cancer tissues in a lever, encephalic malignant tumors and cancer tissues in a breast.

The scattering particles contained in the scattering layer are basically the same as the above mentioned scattering particles in the above mentioned emitter 20H. However, the particles, which can not make a film when they melt, are not suitable; thus, ceramic particles are generally used for the scattering particles.

Further, if desired, surface layers might be formed on the surfaces of the above mentioned several kinds of emitters or the surfaces of the above mentioned scattering surface layers covered on the cores 50A of FIG. 26 respectively to give a large scattering effect. This surface layer contains light scattering particles, which have the larger refractive index than that of the material of the emitter or that of the above mentioned synthetic resin material. For example, sapphire, silicon dioxide, aluminum oxide and the like are used as the scattering particles. Then, the surface layer contains also laser light absorbing particles, which can be included in the emitter as described before, such as carbon and the like. Finally, the surface layer contains a binder, which sticks the particles to each surface and forms a film on the surface as described hereinafter.

Due to the surface layer, the laser light is scattered by the light scattering particles; Further when the laser light impinges on the laser light absorbing particles, the greater part of the energy of the laser light is converted to heat energy.

In so doing, as the vaporization of the tissues is accelerated, the tissues can be incised with the laser light having the low power level of energy penetrated into the emitter. Therefore, when the tissues are incised, the emitter can be moved rapidly. Further, since the required energy of the laser light penetrating into the emitter is low, the medical operation can be carried out quickly with an inexpensive small scaled laser light generator.

On the other hand, referring to the surface layer, if a dispersion containing the laser light absorbing particles and the light scattering particles were coated on the surface of the emitter, after a vaporization of a dispersion medium, the contact of this emitter with the tissues or other substances would cause a damage to the surface layer, because both kinds of particles are attached to the surface of the emitter only by physical adsorptive power.

Therefore, by the binder which sticks the laser light absorbing particles and the light scattering particles to the surface of the emitter, an adhesion of the surface layer to the emitter is enhanced. In this case, the binder is preferably made of light penetrating particles such as synthetic resin particles or ceramic particles such as quartz particles and the like. For forming the film, when the synthetic resin particles are used as the material of the binder, the particles should be melted, or when the ceramic particles having a higher melting point than that of the emitter are used, the surface of the emitter should be melted.

On the other hand, by a following means, the particles can be attached to the surface of the emitter strongly without a binder. For example, the laser light absorbing particles and the light scattering particles are dispersed in a volatile liquid such as alcohol. Then, the above mentioned emitter is dipped into the dispersion. After pulling the emitter from the dispersion, at least the surface of the emitter is heated to a temperature, which is adjacent to the melting point of the light scattering particles. Accordingly, the surface of the emitter is partially melted, thus, the scattering particles are melted to be attached each other and to be attached to the surface of the emitter. Simultaneously, the absorbing particles are included in the melted layer of the scattering particles to form the surface layer without the binder.

Further, by forming a rough surface on the surface of the emitter or by forming the above mentioned surface layer on the rough surface, the laser light can be irradiated more effectively because the laser light is scattered on the rough surface when the laser light is emitted. If desired, the rough surface is formed on the above mentioned core 50A. Further the above mentioned scattering layer might be formed on this rough surface.

As for the diameter of the optical fiber of the present invention, when more than ten optical fibers are buried in the material of the emitter, it is preferably small of 10–200 μm, more preferably 10–100 μm.

While preferred embodiments have been described, it is apparent that the present invention is not limited to the specific embodiments thereof.

What is claimed is:

1. A laser light irradiation apparatus comprising:
    a plurality of optical fibers for transmitting laser light from a laser light generator to a fore end portion of said optical fibers, each optical fiber comprising a core and a clad material around the core, each optical fiber having a base portion which receives and transmits the laser light from the generator and a fore end portion which discharges laser light, wherein
    (i) the base portions of the optical fibers are twisted together in a bundle and along the base portions of the optical fibers the clad materials of all of the optical fibers are bonded together, and
    (ii) the fore end portions of the optical fibers are untwisted and parallel to each other and along the fore end portions of the optical fibers the clad material around each fiber is separate from that of the other optical fibers; and a laser light emitter contacting the fore end portions of the optical fibers to receive the laser light from the fore end portions of the optical fibers for emitting the laser light from all of the fibers.

2. An apparatus according to claim 1 wherein axes of said fore end portions of the optical fibers are arranged in a two-dimensional pattern for laser light irradiation over a two-dimensional surface area.

3. An apparatus according to claim 1, further comprising a surgical handle holding said laser light emitter.

4. An apparatus according to claim 1, wherein said laser light emitter includes a flat surface emitting face.

5. An apparatus according to claim 1, wherein said laser light emitter comprises a pair of laser light emitting elements receiving laser light from the fore end portions of said optical fibers, said light laser emitting elements being arranged so that respective laser light emitting surfaces thereof face each other.

6. A laser light irradiation apparatus as in claim 1, wherein each optical fiber comprises a core and a clad material around the core, and the emitter comprises a clad material similar to the clad material of the fibers.

7. An apparatus according to claim 1, wherein a through-hole is formed along the axis of said laser light emitter.

8. An apparatus according to claim 7, further comprising a flexible guide wire for guiding said laser light emitter inserted through said through-hole.

9. A laser light irradiation apparatus as in claim 1, wherein the emitter comprises a quartz material.

10. A laser light irradiation apparatus as in claim 9, wherein:

at least part of the fore end portion of each fiber core is exposed, and the clad material of the laser light emitter surrounds the exposed fiber cores of the optical fibers.

11. A laser light irradiation apparatus as in claim 1, further comprising a synthetic resin tube surrounding the unified structure along the base portions of the fibers.

12. A laser light irradiation apparatus as in claim 1, wherein the unified structure comprises the clad material along the base portions of the fibers melted and mixed together.

13. A laser light irradiation apparatus as in claim 12, wherein the core of each fiber comprises a quartz material, and the clad material of each fiber comprises a quartz material.

14. A laser light irradiation apparatus as in claim 13, wherein the quartz material of the clad has a different melting point than the quartz material of the cores.

15. A laser light irradiation apparatus as in claim 1, wherein:

at least part of the fore end portion of each fiber comprises of an exposed fiber core, and the laser light emitter comprises a clad material surrounding the exposed fiber cores of the optical fibers.

16. An apparatus according to claim 15, wherein the fore end portions of said optical fibers are substantially parallel to an emitting face of said laser light emitter.

17. An apparatus according to claim 15, wherein said clad material comprises a laser light transmissive synthetic resin material and laser light scattering particles dispersed within the synthetic resin material.

18. A laser light irradiation apparatus comprising:

a plurality of optical fibers for transmitting laser light from a laser light generator to a fore end portion of said optical fibers, each optical fiber having a base portion which receives and transmits the laser light from the generator and a fore end portion which discharges laser light, wherein the base portions of the optical fibers are twisted together in a bundle and the fore end portions of the optical fibers are untwisted and parallel to each other;

a laser light emitter contacting the fore end portions of the optical fibers to receive the laser light from the fore end portions of the optical fibers for emitting the laser light from all of the fibers; and a surface layer formed on at least an emitting face of said laser light emitter, wherein said surface layer comprises laser light absorbing particles and laser light scattering particles which have a larger refractive index than that of said laser light emitter.

19. An apparatus according to claim 18, wherein said light scattering particles have a melting point which is the same as or lower than that of the material of said laser light emitter, a first portion of said scattering particles bonding to the surface of said emitter by melting thereof and a second portion of said scattering particles remaining in an unmelted particulate state to form a scattering layer, said laser light absorbing particles being contained in said scattering layer.

20. An apparatus according to claim 18, wherein said surface layer further comprises laser light transmissive material as a binder for said laser light absorbing particles and said light scattering particles.

21. A laser light irradiation apparatus, comprising:

a plurality of optical fibers for transmitting laser light from a laser light generator to a fore end portion of said optical fibers, each optical fiber having a base portion which receives and transmits the laser light from the generator and a fore end portion which discharges laser light, wherein (i) the base portions of the optical fibers are twisted together in a bundle, (ii) the fore end portions of the optical fibers are untwisted and parallel to each other, and (iii) the fore end portions of the optical fibers are arranged in a line for laser light irradiation along a linear pattern; and a laser light emitter contacting the fore end portions of the optical fibers to receive the laser light from the fore end portions of the optical fibers for emitting the laser light from all of the fibers.

* * * * *